US011045112B2

(12) United States Patent
Reed

(10) Patent No.: US 11,045,112 B2
(45) Date of Patent: Jun. 29, 2021

(54) INCENTIVE SPIROMETER

(71) Applicant: George Reed, Lake Oswego, OR (US)

(72) Inventor: George Reed, Lake Oswego, OR (US)

(*) Notice: Subject to any disclaimer, the term of this patent is extended or adjusted under 35 U.S.C. 154(b) by 78 days.

(21) Appl. No.: 16/162,343

(22) Filed: Oct. 16, 2018

(65) Prior Publication Data

US 2019/0046079 A1    Feb. 14, 2019

Related U.S. Application Data

(63) Continuation-in-part of application No. 14/938,805, filed on Nov. 11, 2015, now abandoned.

(51) Int. Cl.
| | | |
|---|---|---|
| *A61B 5/087* | (2006.01) | |
| *A61B 5/113* | (2006.01) | |
| *A61B 5/08* | (2006.01) | |
| *A61B 5/00* | (2006.01) | |
| *A61M 15/00* | (2006.01) | |
| *A61M 16/00* | (2006.01) | |

(52) U.S. Cl.
CPC .......... *A61B 5/0876* (2013.01); *A61B 5/0004* (2013.01); *A61B 5/08* (2013.01); *A61B 5/113* (2013.01); *A61B 5/7282* (2013.01); *A61M 15/0021* (2014.02); *A61M 15/0086* (2013.01); *A61B 2560/0406* (2013.01); *A61B 2560/0462* (2013.01); *A61B 2562/0219* (2013.01); *A61B 2562/0261* (2013.01); *A61M 2016/0039* (2013.01); *A61M 2205/332* (2013.01); *A61M 2205/3569* (2013.01); *A61M 2205/3592* (2013.01); *A61M 2205/50* (2013.01); *A61M 2205/505* (2013.01); *A61M 2205/584* (2013.01); *A61M 2205/8206* (2013.01)

(58) Field of Classification Search
CPC ......... A61B 5/087; A61B 5/0871; A61B 5/09; A61B 5/0876; A61B 5/08; A61B 5/0816; A61B 5/022; A61B 5/4848; A61B 5/6898; A61B 5/0803; A61B 5/097; A61M 15/00; A61M 15/0065; A61M 15/008; A61M 11/00
See application file for complete search history.

(56) References Cited

U.S. PATENT DOCUMENTS

| | | | | |
|---|---|---|---|---|
| 6,990,975 | B1 * | 1/2006 | Jones | A61M 11/00 128/200.14 |
| 2005/0274378 | A1 * | 12/2005 | Bonney | A61M 15/0048 128/200.23 |
| 2006/0231090 | A1 * | 10/2006 | King | A61M 11/002 128/200.14 |
| 2013/0192597 | A1 * | 8/2013 | McKinnon | A61M 16/0078 128/203.28 |
| 2016/0082208 | A1 * | 3/2016 | Ballam | A61M 16/024 128/200.14 |
| 2017/0216539 | A1 * | 8/2017 | Huber | A61B 5/4845 |

* cited by examiner

*Primary Examiner* — Daniel J Colilla
(74) *Attorney, Agent, or Firm* — Mark S. Hubert

(57) ABSTRACT

A respiratory therapy device that is adapted to matingly connect with two standardized respiratory devices simultaneously to allow for combination, enhanced, single device, respiratory treatments. It monitors the number of PEP treatment events utilizing a motion sensor, and presents a resettable, visual stimulus for each event as well as providing a record of the events in each therapy cycle.

12 Claims, 5 Drawing Sheets

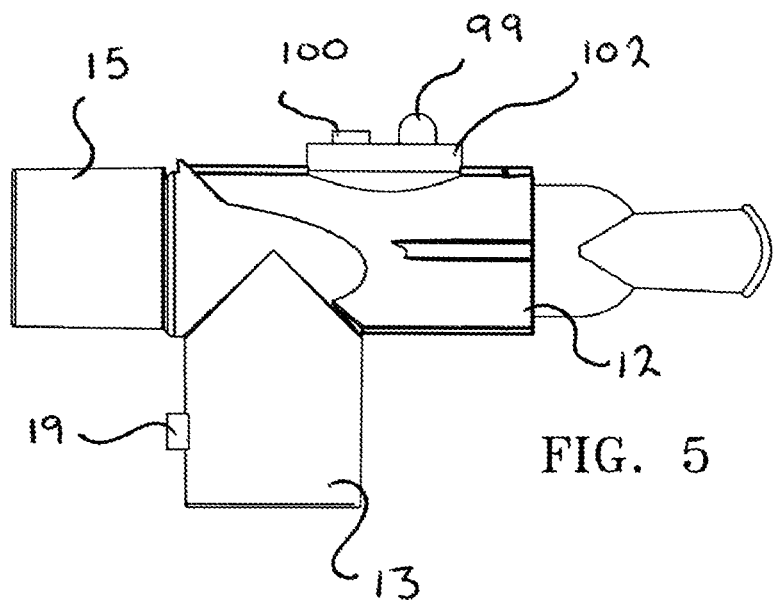
FIG. 5
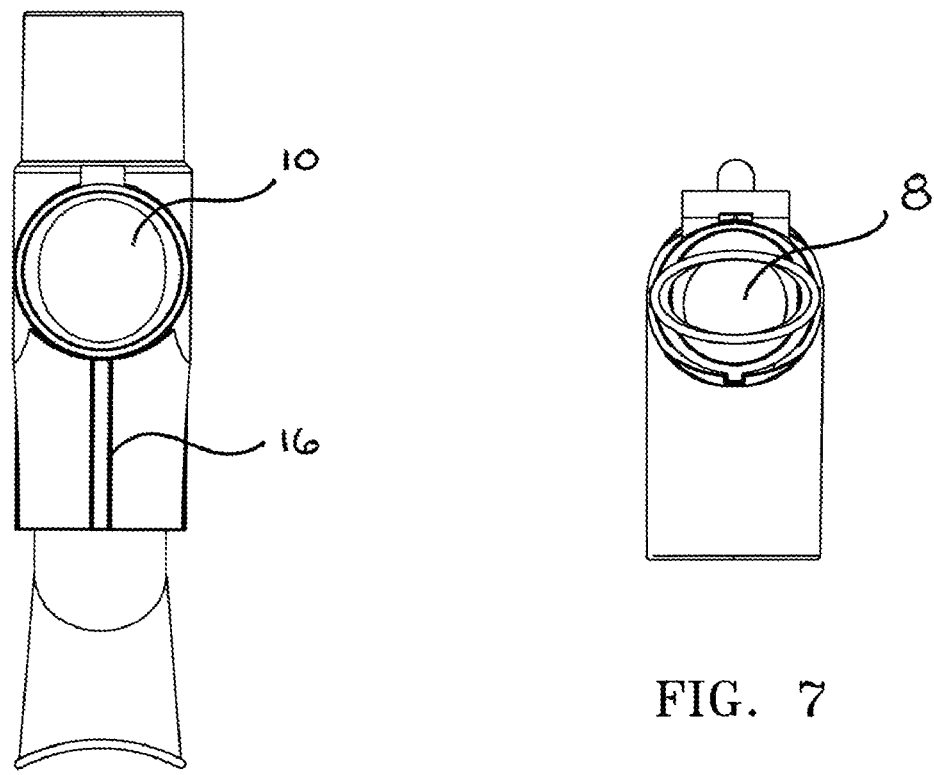
FIG. 6
FIG. 7

INCENTIVE SPIROMETER

CLAIM FOR DOMESTIC PRIORITY

This application incorporates in its entirety, and claims the benefit of priority from pending U.S. Utility patent application Ser. No. 14/938,805 filed Nov. 11, 2015 and entitled "RESPIRATORY MEDICAMENT AND THERAPY DATA SYSTEM AND METHOD OF USE".

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to medical respiratory devices, and more particularly to respiratory patient incentive spirometer technology.

BACKGROUND

The present invention relates to a novel design for a respiratory device capable of engaging multiple respiratory therapy devices. It enables a new level of efficiency in patience compliance, product delivery and condensation losses for those who need such respiratory therapy treatments.

Respiratory treatments vary considerably as do the different manufacturer's devices used to facilitate the treatments. Generally, the patient undergoes separate regimens of inhalation (drug delivery) and exhalation (positive exhalation pressure) treatments. First, the exhalation treatment requires the patient to exhale through any of a plethora of devices that send a resultant pulsation pressure wave back down into their lungs to dislodge phlegm. Second, once enough cycles have been performed, the patient's breathing ability is improved and they can undergo an inhalation treatment wherein they receive a medicated aerosol (generally inhaled antibiotics, bronchodilators, corticosteroids) to further increase their lung capacity and ease their labored breathing.

This type of respiratory therapy has two drawbacks. First, it is time consuming to perform these two exhalation and inhalation treatments separately, back to back. Second, the patient's, often older and frail, require breaks between treatments, further lengthening the time medical personal is required. The drug delivery is most effective immediately after exhalation treatments are performed.

Prior art the devices that have tried to combine the two types of respiratory therapies have failed in maintaining a high percentage of the flow of the aerosol particles in the desirable 0.5 to 4.5-micron diameter. The aerosol particles are generally not constrained in the aerosol section of the device and are some are lost portion in the exhalation phase where they are swirled around in the device to collide and condense. Others escape because of the open inhalation end when the patient takes their mouth off of the device. Lastly, in devices that utilize a valve system, aerosol particles collide with any valve therein as it opens in the inhalation therapy phase. All three mechanisms reduce the amount of medicated aerosol particles that are delivered to the patient and increase the average size of the aerosol particles delivered.

Positive exhalation pressured devices by themselves are not without their problems. These are quite exhausting for many patients and because of their diminished lung capacity, successful exhalations (events) often leaves them out of breath and gasping for air. Often the patient does not exhale with enough pressure to achieve the desired effect of loosening the phlegm and opening the pulmonary pathways for inhaled drug delivery. In this case the delivered drug does is inadequate. Unfortunately with conventional devices the patient has no way of knowing what the right amount of pressure for their PEP device is.

Lastly, the problem with either the administration of an inhalation drug or the performance of a lung-clearing device is that it is usually performed by the patient because of its high frequency. Patients often do not follow the prescribed routines and often do not perform the correct number or events or perform the events correctly. If no medical personnel are present at the time, then there is no corrective action taken to remedy the treatment.

An improved incentive spirometer that alternately combines inhalation drug delivery with lung clearing exercises, minimizes the time required for conventional respiratory treatments, allows the patient to remove their mouth momentarily from the device without significant aerosol losses, minimizes the amount of aerosol condensing on the devices inner walls, maximizes the aerosol particle size transmission efficiency, and monitors, records and sends a visual prompt when the lung clearing exercises are correctly performed, would fulfill a long felt need in the respiratory treatment industry. This new invention utilizes and combines known and new technologies in a unique and novel configuration to overcome the aforementioned problems and accomplish this.

BRIEF SUMMARY

In accordance with various embodiments, an incentive spirometer that encourages patients to practice the actions prescribed to keep their lungs healthy, is provided.

In one aspect, a device that provides a visual stimulus (a reward) and optional recorded record for successful completion of a single breath event of the lung-clearing exercise in a pulmonary treatment regime is provided.

In another aspect, a device that provides a record of the number of successful single breath completions of a pulmonary treatment regime, is provided.

In yet another aspect, a device that allows alternate treatments of drug delivery and lung clearing events so the patient can get the quickest most efficient treatment is provided.

In yet a final aspect, a device that It enables a new level of efficiency in charting patient progress, medicament delivery, patient follow-up, therapy session data and the like that is adapted to matingly connect with all standardized respiratory devices commonly utilized in all lung and respiratory disease treatment, testing, rehabilitation, medicament delivery and life support devices.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 5 is a right side view of the incentive spirometer;

FIG. 6 is a bottom view of the incentive spirometer;

FIG. 7 is an end view of the mouthpiece end of the incentive spirometer;

DETAILED DESCRIPTION OF CERTAIN EMBODIMENTS

Figure 1:
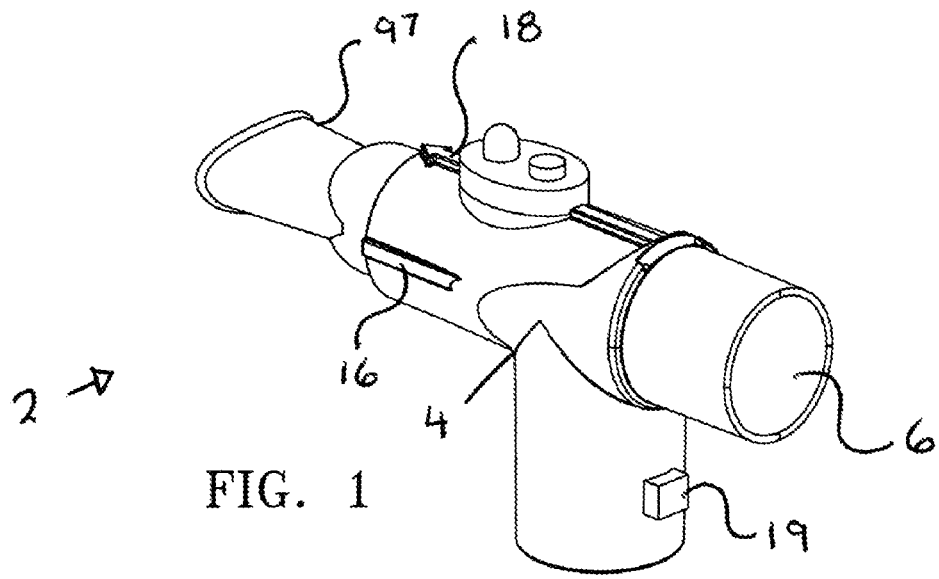
FIG. 1 is a side perspective view of the incentive spirometer.
Figure 2:
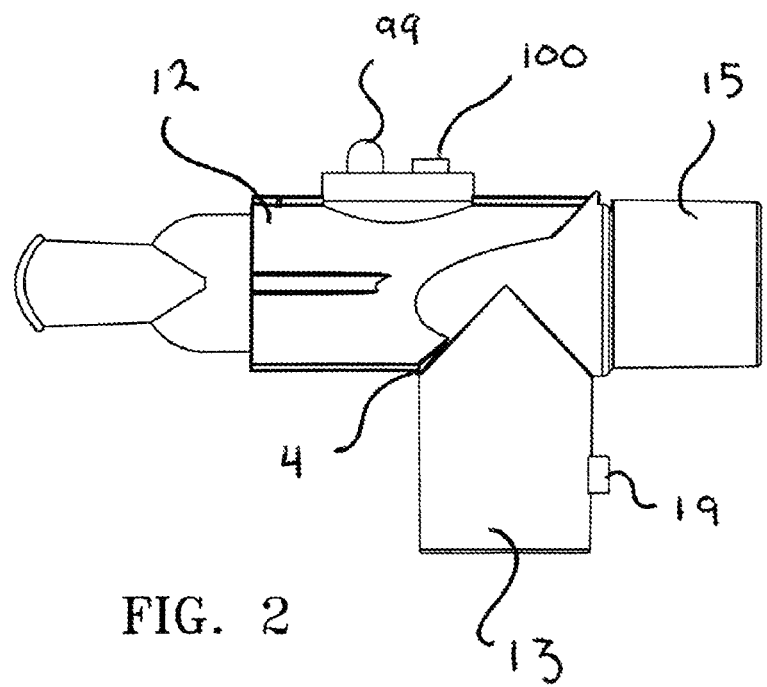
FIG. 2 is a left side view of the incentive spirometer.
Figures 3, 4:
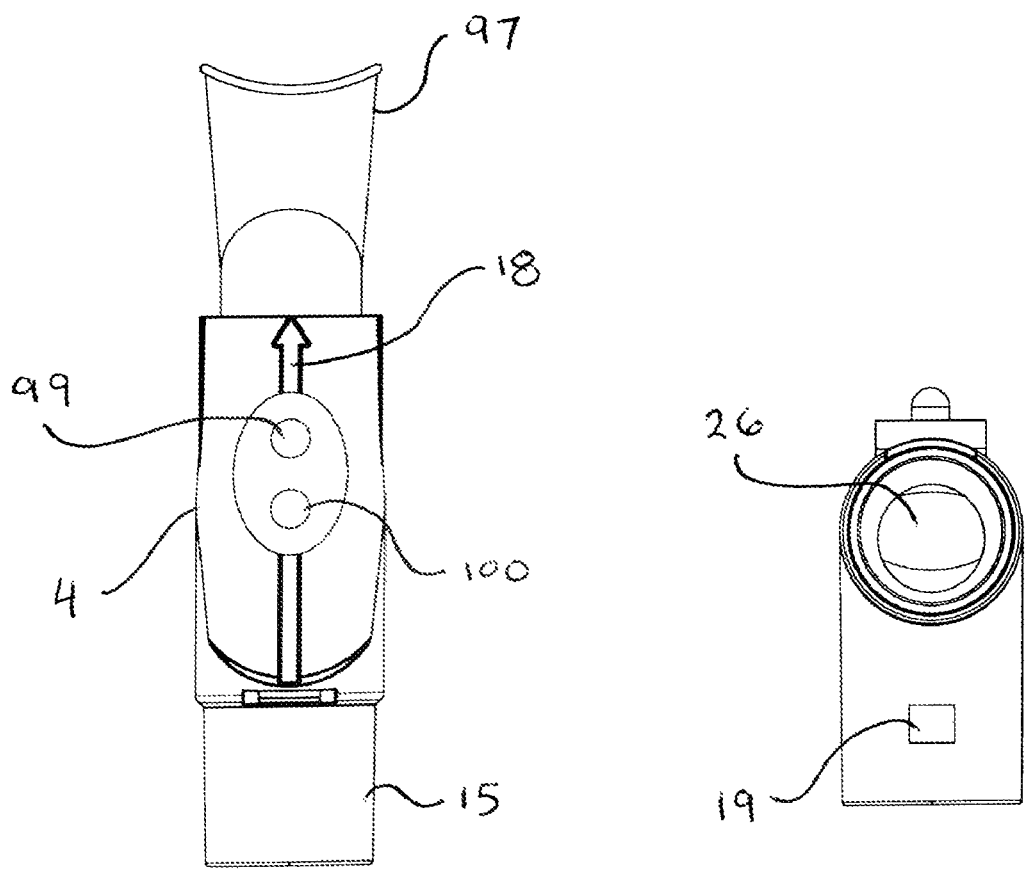
FIG. 3 is a top view of the incentive spirometer.
FIG. 4 is an end view of the nebulizer end of the incentive spirometer.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. It should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the incentive spirometer herein is for the purpose of describing particular embodiments only and is not intended to be limiting of the inventive concept. As used in the description of the incentive spirometer and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "PEP device" refers to a positive expiratory pressure device that provides resistance to the exhalation of breath. This forces respiratory patients to exhale hard into it, increasing the time to empty the lung's capacity against the resistance. This acts as an airway clearance technique to help air get behind the mucus to move it from lung and airway walls. It also holds airways open, keeping them from closing. There are oscillating and non-oscillating PEP devices of varying designs.

As used herein, the term "delivered drug dose" refers to the aggregate amount of aerosol medicament determined to have reached the patient's lungs in a single drug delivery treatment/session. This is can be roughly calculated knowing how many breaths the patient took, the concentration of the aerosol and the efficiency of the drug delivery device considering the aerosol attenuation.

As used herein, the term "inhalation drug delivery device" refers to any one of a group devices that disperse an aerosol or powder pulmonary medicine. These come in various designs such as nebulizers, pressurized metered-dose inhaler (pMDI), and dry powder inhalers (DPIs).

As used herein, the terms "microprocessor" means a computer processor on a microchip that contains all, or most of, the central processing unit (CPU) functions and is the "engine" that goes into motion when the motion sensor sees movement. It may incorporate a real time clock and either or both of volatile/non volatile memory and performs arithmetic and logic operations based on input signals or data from connected devices such as the motion sensor, or manually operated electrical switches (IE to LEDS). It outputs operational signals that integrates with other electrical circuits. It may also output algorithmically derived data to an external computing device. (This may be a local computer, smart phone, or a health provider's network via a remote server.) These operations are the result of a set of instructions that are part of the microprocessor design as is well known in the industry. In simple terms, the microprocessor is a multipurpose, programmable device that accepts digital data as input, processes it according to instructions stored in its memory, and provides results as output. It may have an integrated wireless transceiver.

As used herein, the term "motion sensor" refers to any electo-mechanical device that moves under an external pressure (here, due to a flow of exhaled air passing by it) providing an electric signal to, or switching electricity to a microprocessor upon its movement. Generally, it has a sensing element (motion detector) that is moved by the pressure of exhaled air on it, as it is inserted into the path of movement. Common motion sensors for gasses include Hall effect sensors, heated anemometers, resistive strain sensors, flexible diaphragm pressure switches, swing make or break contact switches and the equivalent.

As used herein, the term "personal mobile device" refers to a device that is both portable and capable of collecting, storing, transmitting or processing electronic data or images. Examples include laptops or tablet PCs, personal digital assistants (PDAs), and "mobile smart" phones. This definition also includes storage media, such as USB hard drives or memory sticks, SD or CompactFlash cards, and any peripherals connected to the device.

As used herein, the term "smartphone" means any web-enabled mobile phone. While the term "smartphone" is well known in the art, smartphones typically include a touch sensitive screen, a messaging client, global positioning systems (GPS) technology or any other geo-position mechanisms to determine the physical coordinates of the smartphone, and a browser application. The browser application employs any web-based language such as JavaScript Object Notation (JSON), JavaScript, HyperText Markup Language (HTML), or any other web-based programming language capable of sending and displaying messages, search queries, and search query results.

The present invention relates to a novel design for an incentive spirometer that will present a pulmonary patient with visual feedback at every event that they successfully complete. It will also optionally, provide a record of this usage for review by medical personnel. It allows the alternating combination of an airway clearance device (here, as an example, a "PEP" device) with an inhalation drug delivery device (that uses an inhalation to deliver a medical powder or aerosol.) This has the benefit of allowing drug delivery and airway clearance to occur in alternating breaths. This ensures that the patient's lungs are as clear as possible to receive the atomized medicine. The drug is delivered as more and more of the phlegm from the patient's lungs is cleared. The rapid delivery of the inhalation drug (generally a beta-agonist bronchodilator) between the patient's forced exhales, prevents the weaker patients from over exhausting their lungs and going into coughing fits or breathing spasms. The design of the incentive spirometer precludes both the incorrect connection of pulmonary devices and the improper operation of the device. The visual feedback and optional tactile interface, serve to communicate to the end user (patient) that they are indeed operating the device properly and garnering its maximum benefits, and the design maximizes the aerosol deliver along the device. The medical practitioner can calculate the delivered drug dose knowing the number of successful events per cycle.

Currently patients with lung disorders and respiratory ailments undergo testing, medicament delivery, monitoring, phlegm dislodgment therapy, lung expansion therapy and other related medical procedures. Many of these are done in the hospital under medical supervision, while others are done unsupervised at home or are used in a hospital in conjunction with a ventilator. This may be a simple as a nebulizer aerosol medicament session or a PEP regime done at home. The problem the results of these go uncharted and possibly may be orally reported. The overall actual physical results of these are often charted however there is no ongoing record of each of these occurrences and what actually transpired on a lung inhalation basis for future trending analyses. This is a huge downfall of respiratory disorder treatment. Because they occur so frequently and often unsupervised, the overall effect or progress of these treatments is not always discernable, even to those medically trained in the industry. One reason, is that the patient is incorrectly using or bypassing their PEP device therapy. They may not know that they are using it wrong or they just may not be able to generate enough pressure in their exhaust breath. Alzheimer's patients frequently need retraining in how to conduct their personal treatments. The inability of the respiratory disease treatment industry to tabulate the actual medicament delivered to a patient's lungs, or how often they actually and correctly, used their PEP device is a huge downfall that this positive inhalation spirometer can remedy.

The incentive spirometer, provides a respiratory medicament and therapy data system that can reward the patient with a visual stimulus upon correct usage and also provides respiratory data to reflect the therapy sessions and treatments conducted.

Looking at FIGS. 1 to 7, it can be seen that the incentive spirometer 2 has a Tee shaped body 4 with three generally circular port openings. The aerosol delivery port 6 and the patient port 8 reside centered about the same horizontal axis, providing a straight, minimal resistance pathway for inhaled drug delivery. (This common centerline is the linear drug delivery path.) In the preferred embodiment, the positive exhalation pressure (PEP) port 10 resides centered about a vertical axis that intersects the horizontal axis at its approximate midpoint. Thus, here, the centerline of the PEP port 10 resides at 90 degrees from the common centerline of the patient port 8 and the aerosol delivery port 6. In this way as can be seen in FIGS. 2 and 5, the PEP port 10 resides approximately equidistant from the patient port 8 and the aerosol delivery port 6. It is known that in alternate embodiments, different acute or obtuse angles may be introduced at the interface of the PEP port end 13 to increase or decrease the PEP resistance.

The drug delivery port 6 is designed for connection to an inhalation drug delivery device and is sized to the industry standard ISO 22 mm circular outer diameter for connection with industry standard nebulizers and similar functioning devices. The outer surface of the drug delivery port end 15 of the body 4 is circular and unadorned.

The patient port 8 is designed to accept a standardized replaceable mouthpiece 97 and it has an ISO 18 mm circular inner diameter. The outer surface of the patient port end 12 of the body 4 is oval and has a series of four horizontal linear ridges 16 equally arranged at a 90 degree radial separation about the surface. On its top top ridge is an arrow 18 at its end pointing toward the patient. The combination of the oval exterior configuration, the horizontal ridges 16 and the arrow 18 are intended to present an obstacle and a visual reminder to ensure improper connections and use of the incentive spirometer 2.

The PEP port 10 is designed for connection to a PEP device and is sized to the industry standard ISO 22 mm circular inner diameter for connection with industry standard PEP devices. The outer surface of the PEP port end 13 of the body 4 is circular and unadorned except for part of the motion sensor 19, which extends therefrom its cylindrical outer surface.

On the body 4 of the incentive spirometer 2, preferably between the patient port end 12 and the drug delivery port end 15 is an exterior housing 102 that contains a battery 104, a microprocessor 106, a light 99 and a reset button 100, the last two which protrude through the exterior housing 102. In the enhanced version, the microprocessor may have an incorporated wireless transmitter. These housed components are operationally connected to the motion sensor 19 either wirelessly or via hard wires. While the preferred location of the exterior housing 102 is the top of the body 4 for ease of tactile operation, the external housing 102 may optionally be located on the PEP port end 13 and incorporate the motion sensor 19 therein (not illustrated).

There are three different embodiments related to the use and placement of the motion sensors on the incentive spirometer. These are best seen with reference to FIGS. 8 to 11. The device may be utilized with one motion sensor or two motion sensors and the sensors may be placed in the PEP port end 13, the patient port end 12 or both ends. The motion sensors may be of various designs such as Hall Effect sensors, mechanical sensors, strain gauges or any equivalent member who's movement can generate an electric signal.

Figure 9:
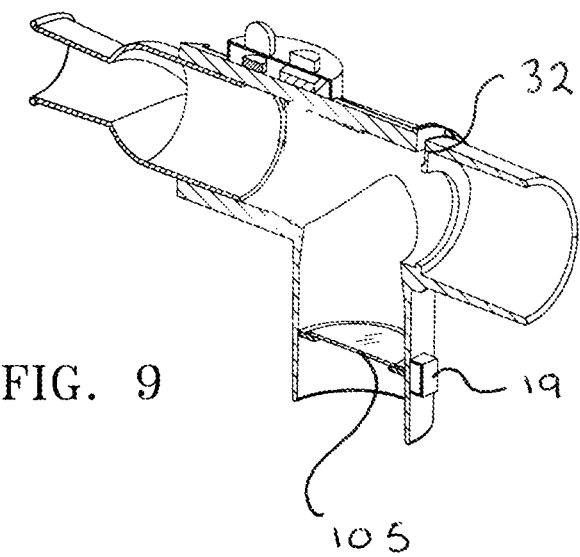
FIG. 9 is a perspective left side cross sectional view of the preferred embodiment incentive spirometer.
Figure 11:
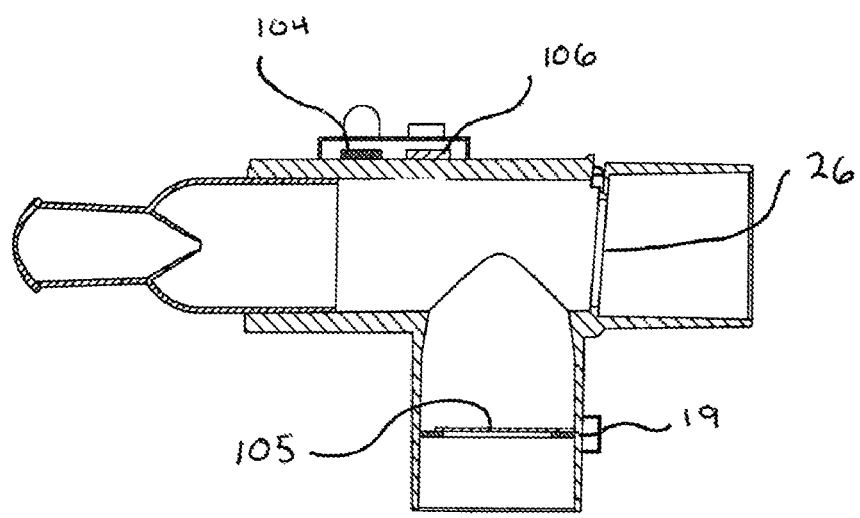
FIG. 11 is a side cross sectional view of the preferred embodiment incentive spirometer with the second embodiment motion sensor.

FIGS. 9 and 11 show the preferred embodiment using a single mechanical movement sensor with a simple mechanical swing motion detector 105 located in the PEP port end 13 across the diameter of the body 4. Upon the contact of a flow of exhaust breath to the detector 105, its lightweight body swings out the way allowing the exhaled breath to pass through the PEP device. As it does this, the motion detector 105 changes the status of an electrical circuit in the motion sensor 26 triggering the motion sensor to send a successful event signal to the microprocessor 106. This mechanical movement sensor may use a magnet on the detector 105 that signals its movement to a Hall Effect sensor at the motion sensor 105. It may also be as simple as a physical make or break electrical set of contacts opened or closed at the motion sensor 26 by the movement of the motion detector 105.

Figure 8:
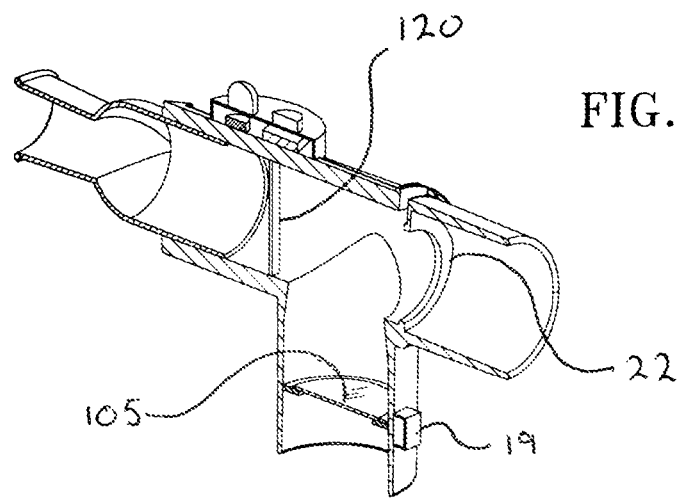
FIG. 8 is a perspective left side cross sectional view of an alternate embodiment incentive spirometer.
Figure 10:
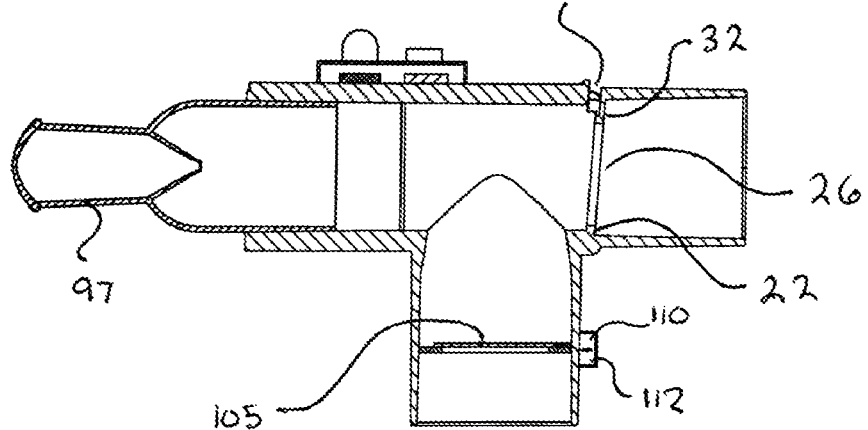
FIG. 10 is a side cross sectional view of an alternate embodiment incentive spirometer.

FIGS. 8 and 10 show the first alternate embodiment with an additional strain gauge detector 120 located in the inhaled drug delivery path of the device, in the patient port end 12 between the patient port 8 and the PEP port 10. It is directly connected to the microprocessor 106 in the external housing. Here the second motion detector 120 is a strain gauge changing its electrical resistance as it is momentarily moved at the initialization of an exhaust breath. In this configuration with two motion sensors, each sensor can be set to move with different forces, thus providing two signals to the microprocessor 106 when successful events take place. This can aid in the therapist's determination of the patient's progress or decline.

Not illustrated is the second alternate embodiment with the motion detector 105 of the first alternate embodiment removed. In this case the second motion detector 120 would initiate the successful event signal. This embodiment has the advantage of simplified electronics as it would be directly connected to the microprocessor 106 and would not require the motion sensor 19 at the PEP end 13. As can be seen, the motion detection can take place at various locations in the incentive spirometer.

When the motion sensor 19 detects motion caused by movement of its motion detector 105, (resulting from sufficient exhalation pressure being exerted along the PEP port end 13), it sends a signal to the microprocessor 106 which illuminates the LED 99 until the reset button 100 is depressed and optionally, logs into memory that a successful single event has occurred within this therapy cycle. If this signal is sent wirelessly, the motion sensor will incorporate a wireless microprocessor transmitter 110 powered by a battery 112. This signal may also be sent through a hard wire routed between the motion sensor 19 and the microprocessor 106, or in the alternate embodiment, the motion sensor 19 may be incorporated into the external housing and directly connected to the microprocessor 106.

The motion sensor 19 may be biased to only send a signal to the microprocessor when events exceed a specified duration. (IE the motion detector stays moved or deflected for more than 5 seconds.) In other embodiments, there may be a preset physical bias against the movement of the motion sensor's detector. This bias would only allow the motion detector 105 to move upon a preset amount of applied force. Successful events are stored in memory as a respiratory treatment cycle, as determined by the microprocessor, based on the time between successful events. These events can then be transmitted wirelessly either as a stand-alone successful cycle or as part of a respiratory cycle to a wireless signal receiving device such as a therapist's smartphone. In the simplest, basic embodiment, the incentive spirometer 2 only signals the occurrence of exhaust breath events. In the enhanced version, the incentive spirometer 2 tracks these occurrences, compiles them in memory into a session history and disseminates sends this data wirelessly.

The motion sensors are only affected during exhalation not inhalation as the resistance offered by the connected PEP device essentially precludes any flow of air in the reverse direction up the PEP port end 13 of the device. Further, the straight path the drug delivery follows between the drug delivery port 6 and the patient port 8 offers little frictional resistance to the flow of the inhaled drug on the patient's inhalation.

Still looking at FIGS. 8 to 11 it can be seen that the drug delivery end 15 of the body 4 has a flapper hinge horn slot 20 cut into its top surface that resides between the aerosol delivery port 6 and the PEP port 10. (The valve flap has been removed in FIG. 8 for clarity.) Between the horn slot 20 and the aerosol deliver port 6, extending normally from the circular inner wall of the body 4 is an angled flapper valve seat 22 that is suspended from a neck 32. (Best seen in FIGS. 8 and 10 and 6) The valve seat 22 is circular and has a circular opening and while the center point of the valve seat 22 lies on the but its center point lies below the common horizontal axis that the aerosol delivery port 6 and the patient port 8 are centered about, the circular opening is offset on the valve seat 22 such that the center point of the circular opening lies below this horizontal axis. Across the opening of the valve seat 22 there may be an optional excessive exhaust exhalation brace (as disclosed in U.S. Utility patent application Ser. No. 14/848,060, incorporated by reference) to prevent the reverse movement of the flapper valve 26 beyond the sealing face 28 of the valve seat 22 towards the aerosol delivery port 6. Although depicted as an "X" brace it may have other configurations as is well known in the industry.

The final component of the incentive spirometer 2 is the flapper valve 26. This valve is critical as it ensures that exhaled breath is directed into the PEP device and that inhaled breath has a low resistance to draw the drug to be delivered into the patient's lungs. The flapper valve in the preferred embodiment is disclosed in U.S. Utility patent application Ser. No. 14/848,060, incorporated by reference although in alternate embodiments it may be of a plethora of simple swing flap designs.

In the preferred embodiment the flapper valve 26 has a valve flap, a neck, a hinge horn and an installation tab. The valve flap is gravity hung by the frictional engagement of the hinge horn in the flapper hinge horn slot. The neck is the hinge mechanism that the valve flap swings on. The neck allows the valve flap to gravity hang into the valve body with enough spatial clearance so that no part of the valve flap touches any art of the interior wall of the body 4. In this way the flapper valve 26 is a very low pressure actuated valve. The neck defines a length between the hinge horn and the valve flap that is less than the distance that the offset valve seat extends from the interior wall of the body 4. The opening pressure is dependent on the weight of the valve flap itself The valve flap has a thickness that is less than the height that the valve flange extends from the interior wall of the] body 4. This design allows for the valve flap to swing completely horizontal by the neck so that it resides behind the valve seat and out of the way of the incoming medicated aerosol during the inhalation cycle. In the preferred embodiment the valve flap is made of medical silicon and its thickness is selected to be the minimum adequate to prevent distortion and allow the valve flap to remain planar to make a proper seal through its service life.

The flapper valve 26 is replaceable if the need arises. To install, the flapper valve 26 is fed horizontally through the patient port 8 and the detachable installation tab is fed up through the flapper hinge horn slot 20 until the hinge horn contacts the top of the incentive spirometer's upper inner wall and the flapper hinge slot 20. The hinge horn is dimensionally wider than the inside opening of the horn slot 20 and will not pass. The installation tab, now on the outside of the incentive spirometer 2 is rocked side to side as tension away from the incentive spirometer 2 is applied so as to pull each side of the horn up through the inside opening of the horn slot 20. (The flapper valve is elastically deformable and in the preferred embodiment is made of a medical grade silicon.) The outside opening of the horn slot 20 is larger than the inside opening and is sized to retain the hinge horn within it such that when the installation tab is cut of at the top of the hinge horn, the hinge horn will remain flush with the outer surface of the incentive spirometer 2. The installation tab is now detached and valve flap now remains hung by its neck which forms the single suspension point that would allow it to freely hang by gravity into the interior cavity of the incentive spirometer 2 such that its planar face resides vertical with respect to the longitudinal axis that passes through the midpoint of the aerosol delivery port 6 and the patient port 8.

As can be seen in FIGS. 10 and 11, the flapper valve seat 22 is angled with its bottom toward the patient port 8. With the bottom of the seat 22 angled forward slightly from the suspension point of the valve flap (the horn slot 20) it allows the circular peripheral edge of the valve flap to contact the circular offset flange of the valve seat 22 enabling a one way, gravity operated seal that is closed upon exhalation pressure from the patient port 8 and opened upon inhalation pressure from the patient port. The optional excessive exhalation brace prevents excessive exhalation pressure from forcing the valve flap beyond the patient port side of the valve seat 22.

The valve seat 22 is offset horizontally from the common linear axis that the aerosol delivery port 6 and the patient port 8 are centered about. This allows room for the valve flap to swing open fully upward to contact the upper inner wall of the incentive spirometer 2 so as to be behind the valve seat 22 and out of the flow of the aerosol particles traversing from the aerosol delivery port 6 to the patient port 8, thereby minimizing any particle collision condensation.

During a therapy session, when the patient stops inhaling the valve flap of the flapper valve 26 swings closed by the effect of gravity (gravity closed valve.) When the patient exhales, the valve flap is forced into an even tighter seal with the valve seat 22 and the patient's lung air is directed down through the PEP port 10 wherein an oscillatory pulsation wave of air pressure is transmitted to the patient's lungs. The rushing air travelling down the PEP port end 13 causes the motion detector 105 to move causing the motion sensor 19 to send a successful event signal to the microprocessor 106 that illuminates the light 99 and optionally stores this event's occurrence in memory for later transmission. During this time any medicated aerosol generated at the drug deliver port 6 is built up and contained in the closed off section of the incentive spirometer body 4 between the valve flap and the drug delivery port 6. The patient may now inhale such that the valve flap will open, out of the path of the aerosol particle stream allowing a does of medicine into their lungs.

The flapper valve 26 provides three methods of minimizing losses. First, it opens completely out of the aerosol pathway because of its minimized weight and the offset valve seat 22. Second with the valve closed on the exhalation cycle, it prevents any of the aerosol from swirling with the exhaled air and escaping through the PEP device. Third, with the valve normally closed by gravity and the angled valve seat 22, the patient can take his mouth off the mouthpiece 97 to spit phlegm without the medicated aerosol escaping from the incentive spirometer 2 because the aerosol is contained between the valve and the aerosol delivery port 6.

The incentive spirometer 2 allows the operation of a dual cycle respiratory therapy without degrading the size of the medicated aerosol particles of reducing the size of the medicated dose. (0.5 to 4.5 microns is the desired mean medicated aerosol particle size.) Additionally, studies have shown that use of a holding chamber or spacer, can increase the medicated aerosol delivery by as much as 36%. Thus optimal performance of the nebulizer is enhanced by the holding chamber created between the closed valve and the medicated aerosol port 6 that collects the non pressurized plume of aerosol medicine and disperses it to the patient.

In operation, the incentive spirometer 2 (with its one way integrated valve) when connected at its aerosol delivery port 6 to a medical aerosol nebulizer and at its PEP port to a positive exhalation pressure respiratory therapy device, will allow the patient to receive alternating cycles of PEP pressure to loosen the phlegm in their lungs followed by medicated aerosol inhalation. Repeated light illumination upon the correct operation of the PEP device helps ensure the patient does not cheat or skip PEP treatments. The storage of the events in a respiratory treatment cycle helps respiratory therapists track their patient's progress. The use of one or more motion detectors in combination with biased motion sensor signaling and stiffened motion detectors allows for multiple diagnostic inferences based on reported data.

The combination of alternating inhaled drug delivery and PEP treatment is a more effective and faster way to provide respiratory therapy to a patient. The tapered oval configuration of the PEP port 10 allows for an extra secure connection with the PEP device which is important because there is a backpressure developed in its use so that the PEP device sees a force trying to dislodge it from the incentive spirometer 2. The four horizontal linear ridges 16 keep the patient from using the wrong end or hooking up the incentive spirometer 2 in reverse.

While certain features and aspects have been described with respect to exemplary embodiments, one skilled in the art will recognize that numerous modifications are possible. Consequently, although several exemplary embodiments are described above, it will be appreciated that the invention is intended to cover all modifications and equivalents within the scope of the following claims.

The invention claimed is:

1. An incentive spirometer for use with an inhaled drug delivery device and a positive exhalation pressure device comprising:

a Tee shaped body having three ends a patient port, a positive exhalation pressure port and an aerosol delivery port, each at one of said ends thereof;

a gravity closed, one way valve operationally disposed within said Tee shaped body, said valve having an open side and a closed side, wherein said patient port and said positive exhalation pressure port are on said open side and said aerosol delivery port is on said closed side, at least one motion sensor having at least one motion detector within said Tee shaped body and located in said open side an external housing, a microprocessor therein said external housing;

an LED light with a light reset button in and extending from said external housing; and a battery therein said external housing;

wherein said battery, said microprocessor, said LED light and said light reset button are in operative communication with said at least one motion sensor to illuminate said LED light when said at least one motion detector experiences a motion due to a patient exhalation event within said Tee shaped body.

2. The incentive spirometer of claim 1 wherein said microprocessor has a real time clock, a memory and a wireless communication transceiver for the storage and transmission of a number of occurrences of said patient exhalation breath events.

3. The incentive spirometer of claim 1 wherein said at least one motion detector is selected from the group of motion detectors including resistive strain sensors, Hall Effect sensors, heated anemometers, flexible diaphragm pressure switches, and swing make or break contact switches.

4. The incentive spirometer of claim 3 wherein the at least one motion sensor has one of said at least one motion detector located in said positive exhalation pressure port of said Tee shaped body.

5. The incentive spirometer of claim 3 wherein the at least one motion sensor has one of said at least one motion detector located in said patient port of said Tee shaped body.

6. The incentive spirometer of 1 wherein the at least one motion sensor has two of said at least one motion detector, one of the two said at least one motion detector located in said positive exhalation pressure port of said Tee shaped body and one of the said at least one motion detector located in said patient port of said Tee shaped body.

7. The incentive spirometer of claim 1 wherein said motion sensor is directly coupled to said external housing and integrated into said microprocessor.

8. The incentive spirometer of claim 1 wherein said aerosol delivery port and said patient port reside centered about a common horizontal axis and said positive exhalation pressure port resides centered about a vertical axis that intersects said horizontal axis at approximately 90 degrees.

9. The incentive spirometer of claim 8 wherein said valve has a flapper valve insert and a valve seat sized for gravitational sealing engagement with said flapper valve insert.

10. The incentive spirometer of claim 9 wherein said valve seat extends inward from an interior surface of said Tee shaped body, and has a center that is offset from said common horizontal axis.

11. The incentive spirometer of claim 10 wherein said valve seat resides at an angle with respect to the said horizontal axis.

12. The incentive spirometer of claim 11 wherein said flapper valve insert has a valve flap connected by a hinge mechanism to a horn, said valve flap suspended by said horn in a slot formed through said Tee shaped body.

* * * * *